United States Patent
Matsukuma et al.

(10) Patent No.: US 8,894,588 B2
(45) Date of Patent: Nov. 25, 2014

(54) GUIDEWIRE AND ABLATION CATHETER SYSTEM WITH BALLOON

(75) Inventors: Akinori Matsukuma, Otsu (JP); Motoki Takaoka, Otsu (JP); Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 224 days.

(21) Appl. No.: 13/319,701

(22) PCT Filed: May 18, 2010

(86) PCT No.: PCT/JP2010/058318
§ 371 (c)(1),
(2), (4) Date: Nov. 10, 2011

(87) PCT Pub. No.: WO2010/134504
PCT Pub. Date: Nov. 25, 2010

(65) Prior Publication Data
US 2012/0065624 A1 Mar. 15, 2012

(30) Foreign Application Priority Data

May 19, 2009 (JP) .................. 2009-120999

(51) Int. Cl.
*A61B 5/00* (2006.01)
*A61M 25/00* (2006.01)
*A61B 18/14* (2006.01)
*A61M 25/09* (2006.01)
*A61B 17/22* (2006.01)
*A61B 18/00* (2006.01)

(52) U.S. Cl.
CPC ............ *A61M 25/09* (2013.01); *A61B 18/1492* (2013.01); *A61M 2025/09183* (2013.01); *A61M 2025/09133* (2013.01); *A61B 2017/22038* (2013.01); *A61B 2018/00285* (2013.01)
USPC .......................................................... 600/585

(58) Field of Classification Search
USPC .......................................................... 600/585
See application file for complete search history.

(56) References Cited

U.S. PATENT DOCUMENTS 4,706,671 A * 11/1987 Weinrib ................. 606/159
5,680,860 A * 10/1997 Imran ..................... 600/374

(Continued)

FOREIGN PATENT DOCUMENTS

| JP | 2002078809 | 3/2002 |
| JP | 2006198209 | 8/2006 |

(Continued)

OTHER PUBLICATIONS

International Application Serial No. PCT/JP2010/058318, International Search Report mailed Jun. 15, 2010, 1 pg.
Supplementary European Search Report for Application No. EP 10 77 7737 dated Nov. 13, 2012.

*Primary Examiner* — Devin Henson
(74) *Attorney, Agent, or Firm* — RatnerPrestia

(57) ABSTRACT

Provided is a guide wire, wherein a deformed portion formed by bending and/or curving the guide wire is located in the region of 20-100 mm from the tip in the longitudinal direction of the guide wire, and in the deformed portion, the shortest distance between the central axis in the longitudinal direction of the guide wire and a point that is the farthest in the direction perpendicular to the central axis is longer than or equal to the minimum inside diameter of a lumen of a catheter shaft of an ablation catheter with a balloon used in combination with the guide wire, and shorter than or equal to 40 mm.

4 Claims, 7 Drawing Sheets

(56) References Cited

U.S. PATENT DOCUMENTS

| | | | |
|---|---|---|---|
| 6,142,994 A | 11/2000 | Swanson et al. | |
| 6,406,442 B1 | 6/2002 | McFann et al. | |
| 7,118,539 B2* | 10/2006 | Vrba et al. | 600/585 |
| 7,435,248 B2* | 10/2008 | Taimisto et al. | 606/41 |
| 7,462,184 B2* | 12/2008 | Worley et al. | 606/129 |
| 2002/0165532 A1* | 11/2002 | Hill et al. | 606/41 |
| 2003/0060821 A1* | 3/2003 | Hall et al. | 606/41 |

FOREIGN PATENT DOCUMENTS

| | | |
|---|---|---|
| JP | 4062935 B2 | 3/2008 |
| WO | WO 99/23958 | 5/1999 |
| WO | WO 00/13735 | 3/2000 |

* cited by examiner

GUIDEWIRE AND ABLATION CATHETER SYSTEM WITH BALLOON

CROSS-REFERENCE TO RELATED APPLICATIONS

This application is the U.S. National Phase application of PCT International Application No. PCT/JP2010/058318, filed May 18, 2010, and claims priority to Japanese Patent Application No. JP2009-120999, filed May 19, 2009, the disclosures of which PCT and priority applications are incorporated herein by reference in their entirely for all purposes.

FIELD OF THE INVENTION

The present invention relates to a guidewire and an ablation catheter system with a balloon.

BACKGROUND OF THE INVENTION

An ablation catheter with a balloon is a medical device to be used for treatment of cardiac arrhythmias such as a paroxysmal supraventricular tachycardia, an atrial tachycardia, an atrial flutter, and a paroxysmal ventricular tachycardia.

An electric isolation of a pulmonary vein with use of the ablation catheter with a balloon (pulmonary venous opening ablation) is conducted by introducing a balloon attached to a front portion of the catheter into an inferior vena cava percutaneously, making the balloon reach a left atrium via an atrial septum from a right atrium of a heart, inflating the balloon, heating a surface of the balloon by radio-frequency power, and ablating an annular periphery of a pulmonary venous opening (Patent Literature 1 and 2).

In the treatment with use of the ablation catheter with a balloon, a guidewire is used to guide the balloon into the pulmonary venous opening and bring the balloon into close contact with the pulmonary venous opening. This guidewire is in a linear shape to enable to pass through a lumen of a catheter shaft easily, and a front portion thereof is elaborated to be formed in a J shape in order to prevent the front portion from damaging a vascularized tissue.

PATENT LITERATURE

Patent Literature 1: Japanese Patent Application Laid-Open No. 2002-78809
Patent Literature 2: Japanese Patent No. 4062935

SUMMARY OF THE INVENTION

It has been discovered that, in the ablation treatment with use of the ablation catheter with a balloon and the guidewire, the front portion of the guidewire itself is heated as well when the balloon is heated, and the front portion of the guidewire sometimes ablates a tissue other than a treatment target region.

The present invention makes it possible to prevent a front portion of a guidewire from being heated erroneously at the time of ablation treatment with use of an ablation catheter with a balloon and the guidewire.

As a result of concerted study directed toward solving the aforementioned problem, the present inventors discovered that a distance between a front portion of a guidewire and a front portion of an ablation catheter with a balloon is advantageously kept to be 20 mm or longer at all times to prevent erroneous heating of the front portion of the guidewire.

That is, the present invention provides a guidewire for an ablation catheter with a balloon including a deformed portion formed by bending and/or curving the guidewire in a 20 to 100-mm region from an end portion in a longitudinal direction of the guidewire, wherein, as for the deformed portion, a shortest distance between a central axis in the longitudinal direction of the guidewire and a point farthest away from the central axis in a direction perpendicular to the central axis is preferably equal to or longer than a shortest inner diameter of a lumen of a catheter shaft of an ablation catheter with a balloon to be used with the guidewire and 40 mm or shorter.

In a case of ablation treatment with use of an ablation catheter with a balloon and a guidewire, it seems that heating of the guidewire itself can be prevented if an operator notices that a front portion of the guidewire is approaching a front portion of the ablation catheter with a balloon. However, at the stage at which the ablation catheter with a balloon has reached a treatment target region in the body, it is impossible to directly see the approach of the front portion of the guidewire to the front portion of the ablation catheter with a balloon, and ablation while the approach is being confirmed on an X-ray fluoroscopic image or the like will impose burdens on the operator and the patient. However, when the above guidewire is used, the front portion of the guidewire is prevented from approaching the front portion of the ablation catheter with a balloon physically, and the front portion of the guidewire can be prevented from being heated before it occurs.

The deformed portion is preferably formed by bending and/or curving the guidewire 2 to 8 times and is more preferably in a spiral shape, a coiled shape, or a lasso shape. Such a deformed portion can prevent the front portion of the guidewire from approaching the front portion of the ablation catheter with a balloon more effectively and can prevent erroneous heating of the front portion of the guidewire more effectively.

The guidewire is preferably provided at the deformed portion with a potential measuring electrode. When the potential measuring electrode is installed to the deformed portion, potential can be measured before and after ablation of a tissue at the treatment target region to enable confirmation of a treatment effect.

Also, the present invention provides an ablation catheter system with a balloon including the above guidewire.

With the present invention, at the time of ablation treatment with use of an ablation catheter with a balloon and a guidewire, a front portion of the guidewire is prevented from being heated erroneously, and a risk of ablating a tissue other than a treatment target region can be reduced. Also, with the present invention, since a distance from the front portion of the guidewire to a front portion of the ablation catheter with a balloon can be kept to be a predetermined distance or longer so as to enable to prevent erroneous heating of the guidewire, and an approach of the front portion of the guidewire to the front portion of the ablation catheter with a balloon can be informed to an operator as feeling through his/her hand, highly safe treatment by the ablation catheter with a balloon can be achieved.

DETAILED DESCRIPTION OF THE INVENTION

Figure 1A:
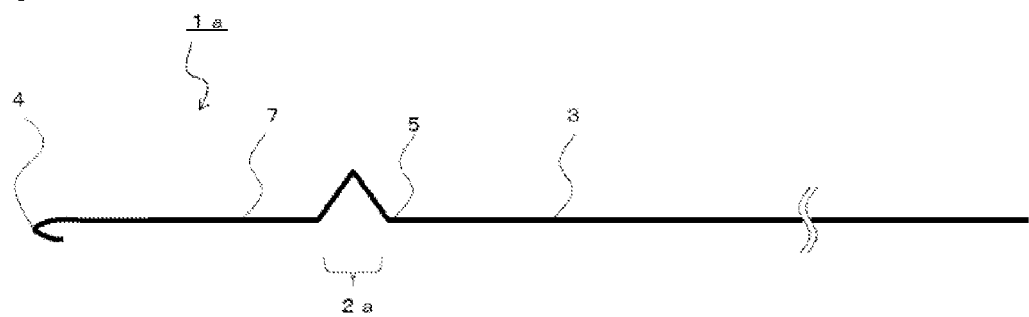
FIG. 1A is a schematic view illustrating a guidewire according to a first embodiment of the present invention.

Preferred embodiments of the present invention will be described below with reference to the accompanying drawings, but the present invention is not limited to these embodiments. Like reference characters denote similar or identical parts throughout the several views thereof, and duplicate explanation is omitted. Also, the ratio in the drawings does not necessarily correspond to an actual ratio.

A guidewire according to embodiments of the present invention is a guidewire for an ablation catheter with a balloon including a deformed portion formed by bending and/or curving the guidewire in a 20 to 100-mm region from an end portion in a longitudinal direction of the guidewire, wherein, as for the deformed portion, a shortest distance between a central axis in the longitudinal direction of the guidewire and a point farthest away from the central axis in a direction perpendicular to the central axis is equal to or longer than a shortest inner diameter of a lumen of a catheter shaft of an ablation catheter with a balloon to be used with the guidewire and 40 mm or shorter.

Figure 1B:
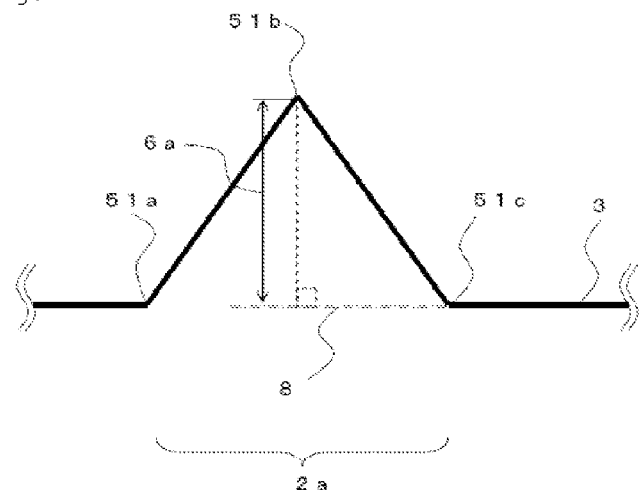
FIG. 1B is a schematic view illustrating a deformed portion of the guidewire according to the first embodiment of the present invention.

FIG. 1A is a schematic view illustrating a guidewire 1a according to a first embodiment of the present invention, and FIG. 1B is a schematic view illustrating a deformed portion 2a of the guidewire 1a according to the first embodiment of the present invention.

The guidewire 1a has on a front side in a longitudinal direction the deformed portion 2a formed by bending and/or curving the guidewire. A near end 5 of the deformed portion 2a is preferably in a 20-mm or longer region from an end portion 4 in the longitudinal direction of the guidewire from a viewpoint of preventing erroneous heating of a front portion of the guidewire and is more preferably in a 20 to 100-mm region from the end portion 4 in the longitudinal direction of the guidewire from a viewpoint of preventing the end portion 4 in the longitudinal direction of the guidewire from damaging a vascularized tissue.

Also, the guidewire 1a has a guidewire main body portion 3 further on a near side than the deformed portion 2a and a guidewire front end straight portion 7 further on the front side than the deformed portion 2a.

The shape of each of the guidewire main body portion 3 and the guidewire front end straight portion 7 is preferably a linear shape.

Examples of a material for the guidewire 1a include a metal such as stainless steel and an alloy, and the guidewire 1a is preferably coated with TEFLON (registered trademark) or the like from a viewpoint of reducing resistance or securing flexibility at the time of insertion.

The length of the guidewire 1a is preferably 0.5 to 2.5 m from a viewpoint of practicality.

Bending stiffness of the guidewire main body portion 3 is a product of Young's modulus of a material for the guidewire main body portion 3 and second moment of area as calculated by Equation 1 shown below and is preferably in a range of 600 to 3700 N·mm².

Bending stiffness=Young's modulus $E$×second moment of area $I$     Equation 1

The bending stiffness of each of the deformed portion 2a and the guidewire front end straight portion 7 is preferably lower than the bending stiffness of the guidewire main body portion 3 in consideration of a risk of damage of a vascularized tissue or the like in a case where a front end of the guidewire 1a contacts the tissue.

The front end of the guidewire 1a is preferably flexible in consideration of a risk of damage of a vascularized tissue or the like in a case of contacting the tissue and is more preferably in a J shape as shown in FIG. 1A.

"The central axis in the longitudinal direction of the guidewire" is a central axis in the longitudinal direction of the guidewire main body portion and corresponds to a central axis 8, which is a central axis in the longitudinal direction of the guidewire main body portion 3 in FIG. 1B.

"The shortest distance from a point farthest away from the central axis in a direction perpendicular to the central axis" corresponds to a deformed portion height 6a, which is a shortest distance from a point farthest away from the central axis 8 in a direction perpendicular to the central axis 8 in FIG. 1B.

The shortest distance from a point farthest away from the central axis in a direction perpendicular to the central axis, that is, the deformed portion height 6a or the like in FIG. 1B, is preferably equal to or longer than a shortest inner diameter of a lumen of a catheter shaft allowing the guidewire to pass therethrough from a viewpoint of allowing an operator who has pulled the guidewire 1a in a near direction to easily recognize that the deformed portion 2 has reached a front end of an ablation catheter with a balloon, and is more preferably equal to or longer than the shortest inner diameter of the lumen of the catheter shaft allowing the guidewire to pass therethrough and 40 mm or shorter in consideration of a diameter of a blood vessel to be ablated.

The guidewire front end straight portion 7 is preferably coaxial with the central axis 8.

The shape of the deformed portion 2a is a shape having bent portions 51a, 51b, and 51c as shown in FIG. 1B.

The number of bent portions of the guidewire 1a shown in FIG. 1B is 3, and the number of bent portions per guidewire is preferably 2 to 8 from a viewpoint of reducing resistance at the time of insertion.

Figure 2A:
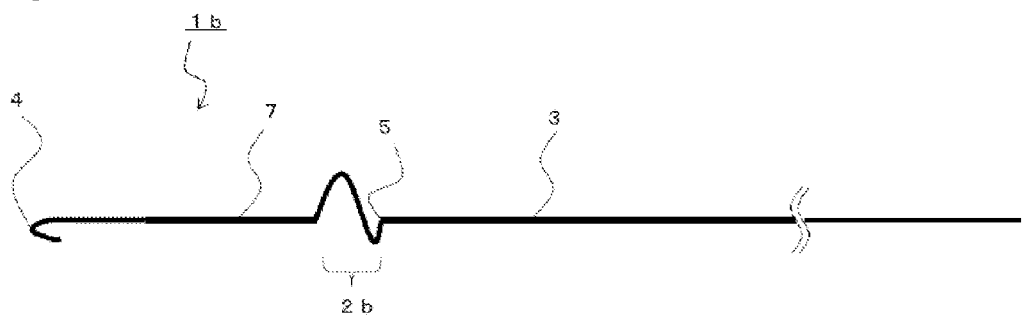
FIG. 2A is a schematic view illustrating a guidewire according to a second embodiment of the present invention.
Figure 2B:
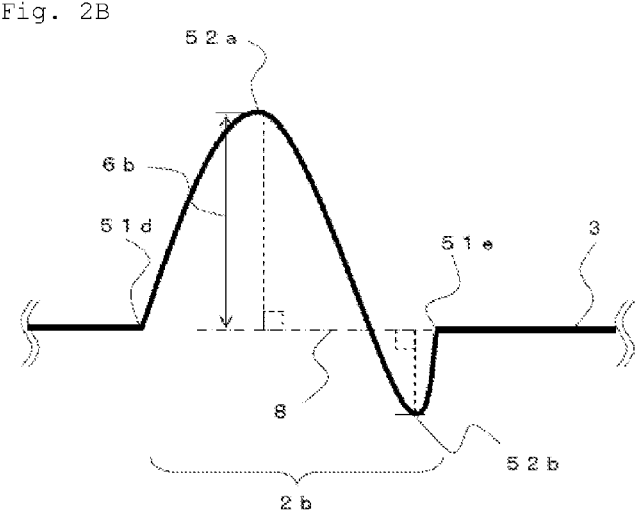
FIG. 2B is a schematic view illustrating a deformed portion of the guidewire according to the second embodiment of the present invention.

FIG. 2A is a schematic view illustrating a guidewire 1b according to a second embodiment of the present invention, and FIG. 2B is a schematic view illustrating a deformed portion 2b of the guidewire 1b according to the second embodiment of the present invention.

Similar to the guidewire 1a, the guidewire 1b has the guidewire main body portion 3 further on the near side than the deformed portion 2b and the guidewire front end straight portion 7 further on the front side than the deformed portion 2b, and the near end 5 of the deformed portion 2b is preferably in a 20-mm or longer region from the end portion 4 in the longitudinal direction of the guidewire and is more preferably in a 20 to 100-mm region from the end portion 4 in the longitudinal direction of the guidewire.

The material, length, and front end of the guidewire 1b and the bending stiffness of the deformed portion 2b are preferably similar to those of the guidewire 1a.

The shape of the deformed portion 2b is a shape having bent portions 51d and 51e and curved portions 52a and 52b or a shape having combination of plural curved portions as shown in FIG. 2B.

The number of bent portions is 2, and the number of curved portions is 2 in FIG. 2B, and the number of bent portions and/or curved portions per guidewire is preferably 2 to 8 from a viewpoint of reducing resistance at the time of insertion.

"The shortest distance from a point farthest away from the central axis in a direction perpendicular to the central axis" corresponds to a deformed portion height 6b in FIG. 2B.

Figure 3A:
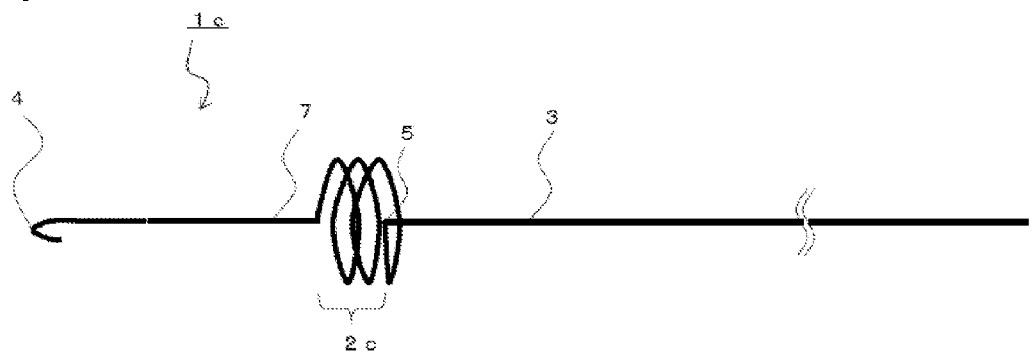
FIG. 3A is a schematic view illustrating a guidewire according to a third embodiment of the present invention.
Figure 3B:
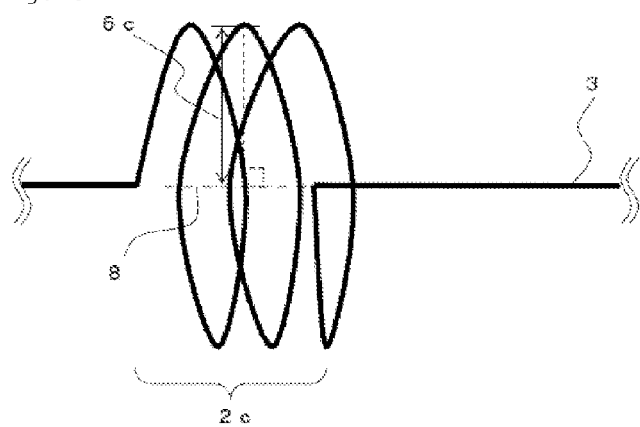
FIG. 3B is a schematic view illustrating a deformed portion of the guidewire according to the third embodiment of the present invention.
Figure 3C:
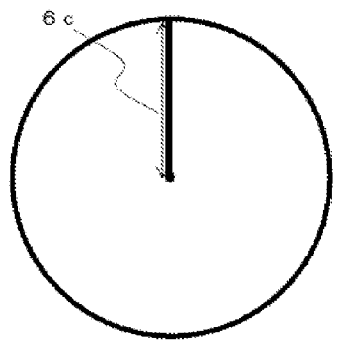
FIG. 3C is a schematic view of the deformed portion of the guidewire according to the third embodiment of the present invention seen in a longitudinal direction of the guidewire.

FIG. 3A is a schematic view illustrating a guidewire 1c according to a third embodiment of the present invention, FIG. 3B is a schematic view illustrating a deformed portion 2c of the guidewire 1c according to the third embodiment of the present invention, and FIG. 3C is a schematic view of the deformed portion 2c of the guidewire 1c according to the third embodiment of the present invention seen in the longitudinal direction of the guidewire.

Similar to the guidewire 1a, the guidewire 1c has the guidewire main body portion 3 further on the near side than the deformed portion 2c and the guidewire front end straight portion 7 further on the front side than the deformed portion 2c, and the near end 5 of the deformed portion 2c is preferably in a 20-mm or longer region from the end portion 4 in the longitudinal direction of the guidewire and is more preferably in a 20 to 100-mm region from the end portion 4 in the longitudinal direction of the guidewire.

The material, length, and front end of the guidewire 1c and the bending stiffness of the deformed portion 2c are preferably similar to those of the guidewire 1a.

The shape of the deformed portion 2c is a spiral shape or a coiled shape as shown in FIG. 3B.

"The shortest distance from a point farthest away from the central axis in a direction perpendicular to the central axis" corresponds to a deformed portion height 6c in FIGS. 3B and 3C.

Figure 4A:
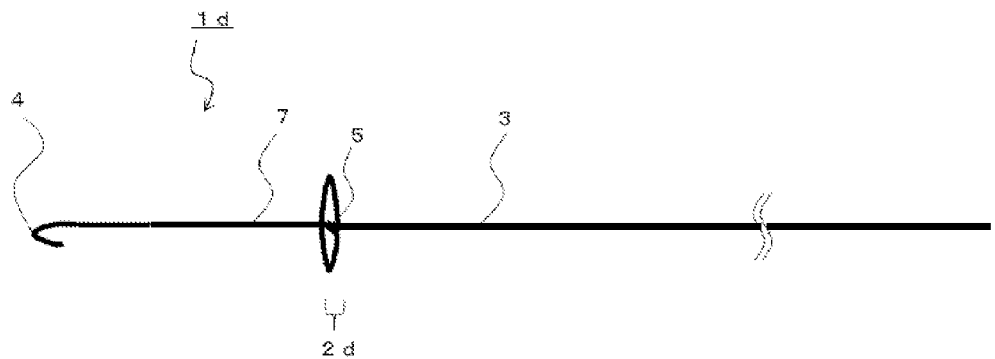
FIG. 4A is a schematic view illustrating a guidewire according to a fourth embodiment of the present invention.
Figure 4B:
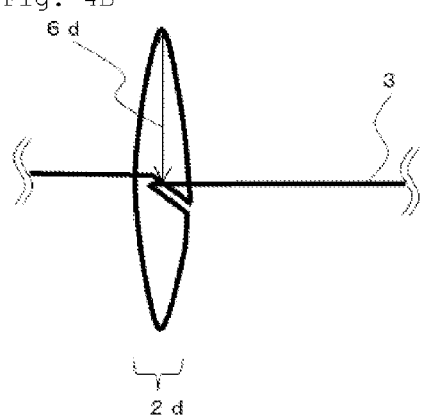
FIG. 4B is a schematic view illustrating a deformed portion of the guidewire according to the fourth embodiment of the present invention.
Figure 4C:
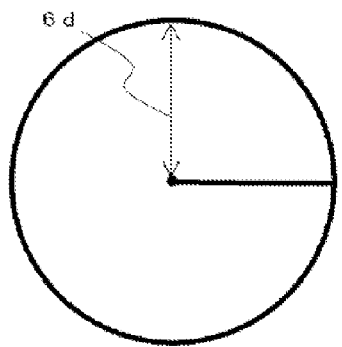
FIG. 4C is a schematic view of the deformed portion of the guidewire according to the fourth embodiment of the present invention seen in the longitudinal direction of the guidewire.

FIG. 4A is a schematic view illustrating a guidewire 1d according to a fourth embodiment of the present invention, FIG. 4B is a schematic view illustrating a deformed portion 2d of the guidewire 1d according to the fourth embodiment of the present invention, and FIG. 4C is a schematic view of the deformed portion 2d of the guidewire 1d according to the fourth embodiment of the present invention seen in the longitudinal direction of the guidewire.

Figure 5A:
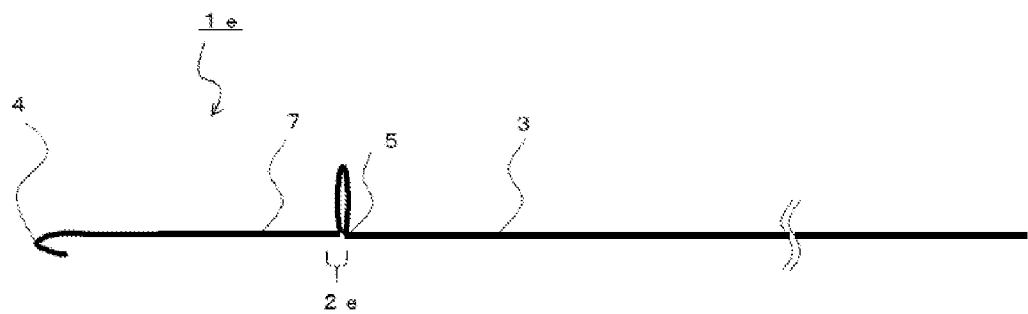
FIG. 5A is a schematic view illustrating a guidewire according to a fifth embodiment of the present invention.
Figure 5B:
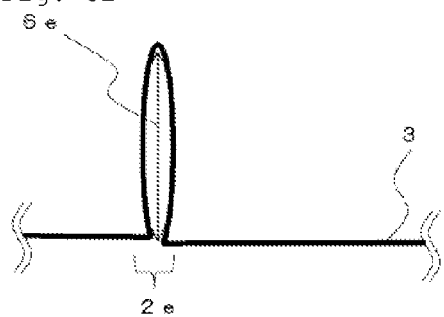
FIG. 5B is a schematic view illustrating a deformed portion of the guidewire according to the fifth embodiment of the present invention.
Figure 5C:
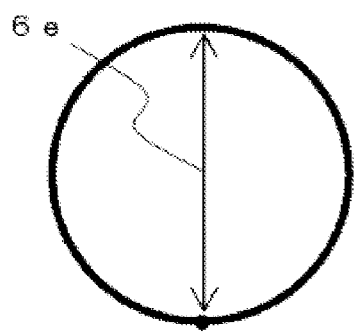
FIG. 5C is a schematic view of the deformed portion of the guidewire according to the fifth embodiment of the present invention seen in the longitudinal direction of the guidewire.

FIG. 5A is a schematic view illustrating a guidewire 1e according to a fifth embodiment of the present invention, FIG. 5B is a schematic view illustrating a deformed portion 2e of the guidewire 1e according to the fifth embodiment of the present invention, and FIG. 5C is a schematic view of the deformed portion 2e of the guidewire 1e according to the fifth embodiment of the present invention seen in the longitudinal direction of the guidewire.

Similar to the guidewire 1a, each of the guidewires 1d and 1e has the guidewire main body portion 3 further on the near side than each of the deformed portions 2d and 2e and the guidewire front end straight portion 7 further on the front side than each of the deformed portions 2d and 2e, and the near end 5 of each of the deformed portions 2d and 2e is preferably in a 20-mm or longer region from the end portion 4 in the longitudinal direction of the guidewire and is more preferably in a 20 to 100-mm region from the end portion 4 in the longitudinal direction of the guidewire.

The material, length, and front end of each of the guidewires 1d and 1e and the bending stiffness of each of the deformed portions 2d and 2e are preferably similar to those of the guidewire 1a.

The shape of each of the deformed portions 2d and 2e is a lasso shape (a throwing rope shape) as shown in FIGS. 4B and 5B.

"The shortest distance from a point farthest away from the central axis in a direction perpendicular to the central axis" corresponds to a deformed portion height 6d or 6e in FIGS. 4B and 4C or FIGS. 5B and 5C.

Figure 6:
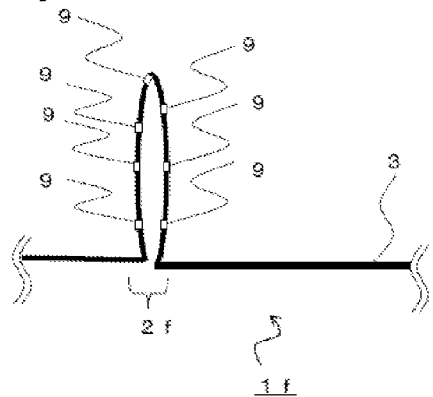
FIG. 6 is a schematic view illustrating a deformed portion of a guidewire according to another embodiment of the present invention.

FIG. 6 is a schematic view illustrating a deformed portion 2f of a guidewire 1f according to another embodiment of the present invention.

Similar to the guidewire 1a, the guidewire 1f has the guidewire main body portion 3 further on the near side than the deformed portion 2f and the guidewire front end straight portion 7 further on the front side than the deformed portion 2f, and the near end 5 of the deformed portion 2f is preferably in a 20-mm or longer region from the end portion 4 in the longitudinal direction of the guidewire and is more preferably in a 20 to 100-mm region from the end portion 4 in the longitudinal direction of the guidewire.

The material, length, and front end of the guidewire 1f and the bending stiffness of the deformed portion 2f are preferably similar to those of the guidewire 1a.

The deformed portion 2f is preferably provided with potential measuring electrodes 9 as shown in FIG. 6 for measurement of potential for confirmation of a treatment effect.

The other end of a potential measuring electrode lead wire connected to the potential measuring electrodes 9 is inserted into an interior of the guidewire 1f and is connected to a potential measuring instrument.

It is to be noted that the potential measuring electrodes 9 can be installed to the deformed portion of the guidewire according to any embodiment.

The number of potential measuring electrodes is preferably 1 to 16 per guidewire and is more preferably 4 to 10.

Also, an ablation catheter system with a balloon according to the present invention has the guidewire according to embodiments of the present invention.

Figure 7:
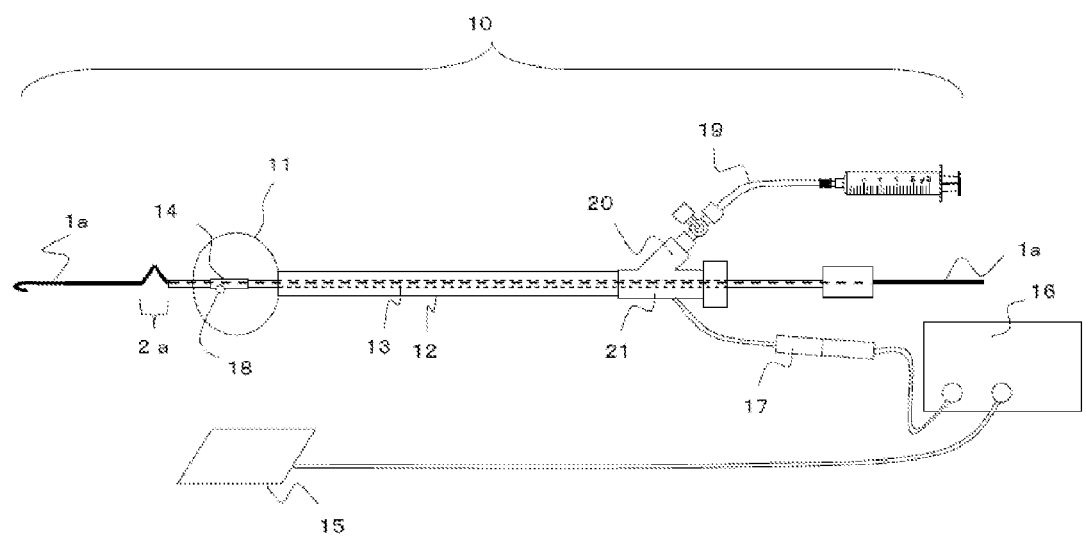
FIG. 7 is a schematic view illustrating an embodiment of an ablation catheter system with a balloon having the guidewire according to the first embodiment of the present invention.
Figure 8:
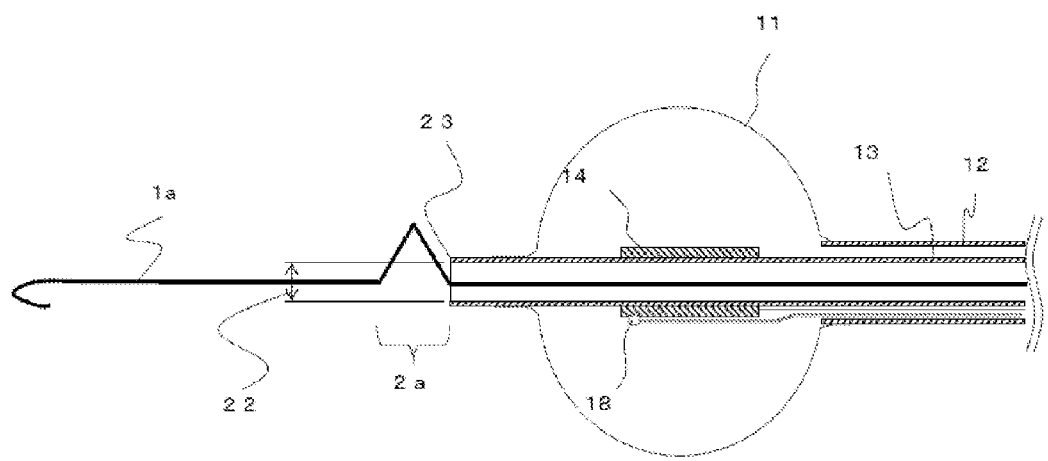
FIG. 8 is a schematic view illustrating a cross-section horizontal to a longitudinal direction of a balloon of the ablation catheter system with a balloon having the guidewire according to the first embodiment of the present invention.

FIG. 7 is a schematic view illustrating an embodiment of an ablation catheter system with a balloon having the guidewire according to the first embodiment of the present invention, and FIG. 8 is a schematic view illustrating a cross-section horizontal to a longitudinal direction of a balloon of the ablation catheter system with a balloon having the guidewire according to the first embodiment of the present invention.

The ablation catheter system with a balloon shown in FIG. 7 has on a front side of an ablation catheter with a balloon 10 a balloon 11 that can inflate and deflate and has a double-cylinder catheter shaft in which an inner side tube body 13 is inserted into a lumen of an outer side tube body 12. A front portion of the balloon 11 is fixed to a front portion in a longitudinal direction of the inner side tube body 13 while a rear portion of the balloon 11 is fixed to a front portion in a longitudinal direction of the outer side tube body 12. It is to be noted that the catheter shaft may be a single-tube shaft, not a double-cylinder shaft, to obtain the effect of the guidewire 1 according to aspects of the present invention.

The length of each of the outer side tube body 12 and the inner side tube body 13 is preferably 0.5 to 2 m and is more preferably 0.8 to 1.2 m.

A material for each of the outer side tube body 12 and the inner side tube body 13 is preferably a flexible material with excellent antithrombogenicity such as a fluorine resin, a polyamide resin, a polyurethane resin, or a polyimide resin.

The shape of the balloon 11 may be any shape as long as it can fit in a blood vessel, and examples of the shape include a spherical shape having a diameter of 20 to 40 mm and a tapered conical outer shape.

The film thickness of the balloon 11 is preferably 20 to 200 µm and is more preferably 30 to 100 µm.

A material for the balloon 11 is preferably a stretchable material with excellent antithrombogenicity and is more preferably a polyurethane polymeric material.

Examples of the polyurethane polymeric material include thermoplastic polyether urethane, polyether polyurethane urea, fluorine polyether urethane urea, a polyether polyurethane urea resin, and polyether polyurethane urea amide.

A radio-frequency carrying electrode 14 is arranged in an interior of the balloon 11.

In a case where the radio-frequency carrying electrode 14 is to be fixed to the inner side tube body 13, examples of a fixing method include caulking, adhesive, welding, and a heat shrinkable tube, but the radio-frequency carrying electrode 14 does not have to be fixed to the inner side tube body 13.

The balloon is heated by supplying radio-frequency power between the radio-frequency carrying electrode 14 and an off-balloon electrode 15 attached to a surface of a patient's body by a radio-frequency generator 16, and plural radio-frequency carrying electrodes 14 may be arranged in the interior of the balloon 11 to supply the radio-frequency power among the radio-frequency carrying electrodes. Also, from a viewpoint of improving flexibility of the balloon in a range in which the radio-frequency carrying electrode 14 has been arranged, the radio-frequency carrying electrode 14 may be divided into plural pieces and arranged.

The shape of the radio-frequency carrying electrode 14 is not particularly limited and is preferably a tubular shape such as a coiled shape or a cylindrical shape.

The diameter of an electric wire of the coiled radio-frequency carrying electrode 14 is preferably 0.1 to 1 mm and is more preferably 0.2 to 0.5 mm from a viewpoint of practicality.

A material for the radio-frequency carrying electrode 14 is preferably a highly conductive metal.

Examples of the highly conductive metal include highly conductive metals such as silver, gold, platinum, and copper.

A radio-frequency power supplying lead wire connected to the radio-frequency carrying electrode 14 is connected to the radio-frequency generator 16 via an electrode connector 17 and transmits radio-frequency currents to the radio-frequency carrying electrode 14.

The radio-frequency power supplying lead wire is connected to the radio-frequency carrying electrode 14 by soldering, caulking, or the like.

The diameter of the radio-frequency power supplying lead wire is preferably 0.1 to 1 mm and is more preferably 0.2 to 0.5 mm from a viewpoint of practicality.

Examples of a material for the radio-frequency power supplying lead wire include highly conductive metals such as copper, silver, gold, platinum, tungsten, and an alloy. The radio-frequency power supplying lead wire is preferably provided with an electrical insulating protective coat such as a fluorine resin from a viewpoint of preventing short circuit, and it is more preferable to form a part of the radio-frequency power supplying lead wire, from which the electrical insulating protective coat has been stripped away, in a coiled shape and use the part as the radio-frequency carrying electrode 14 from a viewpoint of dispensing with connection by soldering, caulking, or the like.

A temperature sensor 18 is fixed to the inner side tube body 13, the radio-frequency carrying electrode 14, or an inner surface of the balloon 11. Plural temperature sensors 18 may be fixed from a viewpoint of backup in a case of a failure of the temperature sensor.

Examples of the temperature sensor 18 include a thermocouple and a resistance-temperature detector.

A temperature sensor lead wire connected to the temperature sensor 18 is connected to the radio-frequency generator 16 via the electrode connector 17 and transmits a temperature signal measured at the temperature sensor 18 to the radio-frequency generator 16.

When the temperature sensor 18 is a thermocouple, a material for the temperature sensor lead wire is preferably the same material as that for the thermocouple, and examples of the material include copper and constantan when the temperature sensor 18 is a Type T thermocouple. On the other hand, when the temperature sensor 18 is a resistance-temperature detector, a material for the temperature sensor lead wire is preferably a highly conductive metal such as copper, silver, gold, platinum, tungsten, or an alloy. Meanwhile, the temperature sensor lead wire is preferably provided with an electrical insulating protective coat such as a fluorine resin from a viewpoint of preventing short circuit.

Also, the ablation catheter with a balloon 10 shown in FIG. 7 has a tube connecting portion 20 having a through hole to which a balloon inflating/deflating tube 19 for supplying a liquid to the interior of the balloon 11 is attached. The tube connecting portion 20 communicates with a space between the outer side tube body 12 and the inner side tube body 13.

The tube connecting portion 20 is preferably provided at the outer side tube body, a stopcock, a cap, or a coupling member arranged on a rear side in the longitudinal direction of the outer side tube body, and the tube connecting portion 20 of the ablation catheter with a balloon 10 shown in FIG. 7 is provided at a coupling member 21.

The radio-frequency power supplying lead wire and the temperature sensor lead wire are preferably inserted into the space between the outer side tube body 12 and the inner side tube body 13 from the radio-frequency carrying electrode 14 and the temperature sensor 18 and arranged so as to be taken outside from the coupling member 21.

The guidewire 1a is inserted into a lumen of the inner side tube body 13.

The shortest inner diameter of the lumen of the catheter shaft allowing the guidewire to pass therethrough corresponds to a guidewire lumen inner diameter 22 in FIG. 8, for example.

When the deformed portion height 6a is the guidewire lumen inner diameter 22 or longer, the deformed portion 2a acts as a resistor at the front end of the ablation catheter with a balloon in a case where an operator intends to pull the guidewire 1a in the near direction from the ablation catheter with a balloon 10, and the operator can easily recognize that the deformed portion 2a has contacted a front end 23 of the ablation catheter with a balloon.

EXAMPLES

Hereinafter, specific examples of the guidewire and the ablation catheter system with a balloon having the same according to the present invention will be described with reference to the drawings.

Example 1

An ablation catheter system with a balloon having the guidewire according to the first embodiment of the present invention was prepared as follows.

A stainless steel wire (SUS304WPB wire) having a cross-sectional shape of a circle with a diameter of 0.6 mm and having a length of 2000 mm was prepared as the guidewire 1a, and the deformed portion 2a having the three bent portions 51a, 51b, and 51c was formed so that the near end 5 of the deformed portion 2 might be arranged at a position 20 mm distanced in length from the end portion 4 in the longitudinal direction of the guidewire, which was an end processed in a J shape (hereinafter referred to as EXAMPLE 1 guidewire). The shortest distance between the central axis in the longitudinal direction of the guidewire 1a and a point farthest away from the central axis in a direction perpendicular to the central axis, that is, the deformed portion height 6a, was 5 mm.

Subsequently, the balloon 11 having a diameter of 30 mm and a thickness of 50 μm was prepared by dipping, in which a balloon mold made of glass having a mold surface corresponding to a desired balloon shape was immersed into a polyurethane solution having a concentration of 13% and was heated to evaporate a solvent to form an urethane polymer film on the surface of the mold.

The coupling member 21 provided with the tube connecting portion 20 was inserted and fitted in a near end of the outer side tube body 12, which was a tube made of polyurethane having an outer diameter of 4 mm, an inner diameter of 3 mm, and an entire length of 1000 mm, and was attached and fixed.

With a position 20 mm distanced from a front end of the inner side tube body 13, which was a tube made of polyurethane having an outer diameter of 1.7 mm, an inner diameter of 1.2 mm, and an entire length of 1100 mm, set as a starting point, after a part of the electrical insulating protective coat provided on the radio-frequency power supplying lead wire, which was an electric soft copper wire plated with silver having a diameter of 0.5 mm, was stripped away, the radio-frequency power supplying lead wire was directly wound around the inner side tube body 13 to form a coiled shape having a length of 10 mm and use it as the radio-frequency carrying electrode 14.

An extra fine thermocouple copper wire provided with the electrical insulating protective coat as one temperature sensor lead wire and an extra fine thermocouple constantan wire provided with the electrical insulating protective coat as the other temperature sensor lead wire were connected at the tip ends and were reinforced by soldering, and the connected portion was used as the temperature sensor 18. The temperature sensor 18 was fixed at a position 3 mm distanced from a front end of the radio-frequency carrying electrode 14 by caulking.

The inner side tube body 13 to which the radio-frequency carrying electrode 14 and the temperature sensor 18 were fixed was inserted into the outer side tube body 12 from a rear side of the coupling member 21 and was fixed to the coupling member 21 by a cap.

The radio-frequency power supplying lead wire and the temperature sensor lead wire were inserted into the space between the outer side tube body 12 and the inner side tube body 13 from the radio-frequency carrying electrode 14 and the temperature sensor 18, were taken outside from the coupling member 21, and were connected to the electrode connector 17.

The front portion of the balloon 11 was fixed on an outer circumference of the inner side tube body 13 at a position 10 mm distanced from the front end of the inner side tube body 13 by thermal welding while the rear portion of the balloon 11 was thermally welded on an outer circumference of a front portion of the outer side tube body 12 to prepare an ablation catheter with a balloon according to the first embodiment of the present invention.

Finally, the balloon 11 was supplied with saline and was inflated so that the maximum diameter thereof might be 30 mm, EXAMPLE 1 guidewire was then inserted into the lumen of the inner side tube body 13 of the ablation catheter with a balloon according to the first embodiment of the present invention, and an ablation catheter system with a balloon having the guidewire according to the first embodiment of the present invention (hereinafter referred to as EXAMPLE 1 catheter system) was completed.

Comparative Example 1

As COMPARATIVE EXAMPLE 1, an ablation catheter system with a balloon was prepared as follows.

A stainless steel wire (SUS304WPB wire) having a cross-sectional shape of a circle with a diameter of 0.6 mm and having a length of 2000 mm was processed in a J shape at an end thereof and was used as a guidewire as it was without forming a deformed portion (hereinafter referred to as COMPARATIVE EXAMPLE 1 guidewire).

Subsequently, the balloon 11 of the same ablation catheter with a balloon as that prepared in EXAMPLE 1 was supplied with saline and was inflated so that the maximum diameter thereof might be 30 mm, COMPARATIVE EXAMPLE 1 guidewire was then inserted into the lumen of the inner side tube body 13, and an ablation catheter system with a balloon (hereinafter referred to as COMPARATIVE EXAMPLE 1 catheter system) was completed.

(Guidewire Front End Temperature Test)

In each of the ablation catheter systems with a balloon prepared in EXAMPLE 1 and COMPARATIVE EXAMPLE 1, the radio-frequency power was supplied from the radio-frequency generator 16 to heat the balloon, and each guidewire front end temperature was measured.

Figure 9:
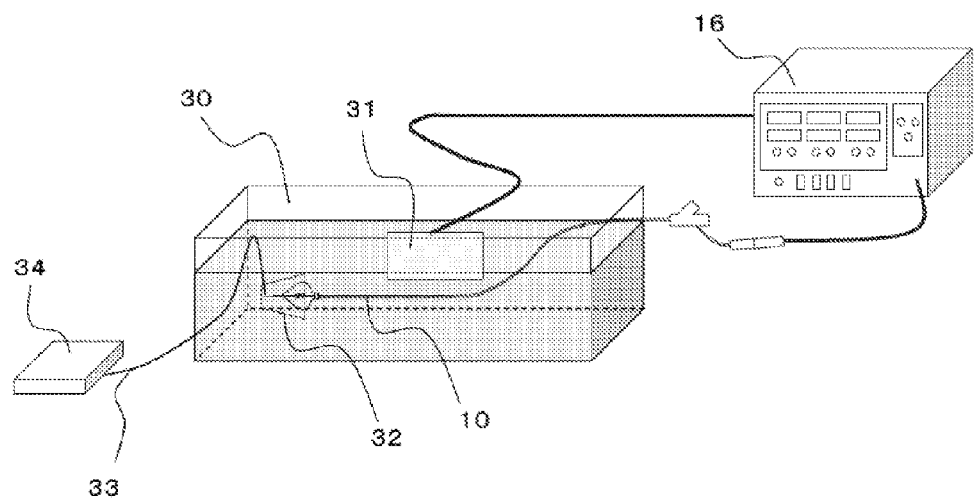
FIG. 9 is a schematic view of a guidewire front end temperature testing system.

FIG. 9 is a schematic view of a guidewire front end temperature testing system. The radio-frequency generator 16 was connected to a counter electrode plate 31, which was an off-balloon electrode attached to an inner wall of a water tank 30, and the water tank 30 was filled with 35 L 0.9% saline at 37° C.

A pseudo affected tissue 32 made of agar into a shape in which the balloon inflated so that the maximum diameter thereof might be 30 mm would be fitted was installed in the water tank 30 so as to be immersed completely in the 0.9% saline, and the balloon 11 of the ablation catheter with a balloon 10 was fitted into the pseudo affected tissue 32.

The front end temperature of the guidewire stuck into the pseudo affected tissue 32 was measured by a Type T thermocouple 33 connected to a temperature data logger 34. The measurement of the guidewire front end temperature was continued for 5 minutes from starting supplying radio-frequency power (frequency: 1.8 MHz, maximum power: 150 W, and setting temperature: 70° C.) by the radio-frequency generator 16, and the maximum temperature of the guidewire front end during the period was regarded as the guidewire front end temperature.

In the test using EXAMPLE 1 catheter system, the guidewire front end temperature was measured after the guidewire 1a was fixed at a position in which the near end 5 of the deformed portion 2a of the guidewire 1a contacted the front end of the ablation catheter with a balloon 10 so that the distance between the end portion 4 in the longitudinal direction of the guidewire 1a and the front end of the ablation catheter with a balloon 10 might be 20 mm. The result is shown in Table 1.

In the test using COMPARATIVE EXAMPLE 1 catheter system, after it was visually confirmed that the distance between the front end of the guidewire and the front end of the ablation catheter with a balloon 10 was 20 mm, 10 mm, or 2 mm, the guidewire front end temperature was measured in each distance. The result is shown in Table 1.

TABLE 1

| Catheter system | Distance between front end of guidewire and front end of ablation catheter with balloon [mm] | Guidewire front end temperature [° C.] |
| --- | --- | --- |
| EXAMPLE 1 | 20 | 40 |
| COMPARATIVE EXAMPLE 1 | 20 | 40 |
|  | 10 | 60 |
|  | 2 | 100 |

As a result of the above experiment, it has been confirmed that, the shorter the distance between the front end of the guidewire and the front end of the ablation catheter with a balloon, the higher the guidewire front end temperature becomes. A preferable ablation temperature by the ablation catheter with a balloon is less than 60° C. When the guidewire front end temperature is 60° C. or higher, the guidewire front portion will ablate a tissue other than a treatment target region, which increases a burden on a patient. Thus, for highly safe ablation, it is clear that the distance between the front end of the guidewire and the front end of the ablation catheter with a balloon is advantageously kept to be 20 mm or longer.

Also, while an operator had to visually confirm that the distance between the front portion of the guidewire and the front end of the ablation catheter with a balloon was kept to be 20 mm or longer in the test using COMPARATIVE EXAMPLE 1 catheter system, the operator easily recognized that the distance between the front portion of the guidewire and the front end of the ablation catheter with a balloon was kept to be 20 mm or longer in the test using EXAMPLE 1 catheter system since the operator who pulled the guidewire in the near direction felt resistance at a position at which the near end 5 of the deformed portion 2 contacted the front end of the ablation catheter with a balloon 10. Accordingly, it is clear that the ablation catheter with a balloon according to aspects of the present invention can achieve highly safe ablation that decreases burdens both on the patient and the operator.

The present invention can be used as an ablation catheter system with a balloon that ablates an affected tissue.

DESCRIPTION OF REFERENCE SIGNS 1a, 1b, 1c, 1d, 1e, 1f . . . guidewire, 2a, 2b, 2c, 2d, 2e, 2f . . . deformed portion, 3 . . . guidewire main body portion, 4 . . . end portion in a longitudinal direction of a guidewire, 5 . . . near end, 6, 6a, 6b, 6c, 6d, 6e . . . deformed portion height, 7 . . . guidewire front end straight portion, 8 . . . central axis, 9 . . . potential measuring electrode, 10 . . . ablation catheter with a balloon, 11 . . . balloon, 12 . . . outer side tube body, 13 . . . inner side tube body, 14 . . . radio-frequency carrying electrode, 15 . . . off-balloon electrode, 16 . . . radio-frequency generator, 17 . . . electrode connector, 18 . . . temperature sensor, 19 . . . balloon inflating/deflating tube, 20 . . . tube connecting portion, 21 . . . coupling member, 22 . . . guidewire lumen inner diameter, 23 . . . front end of an ablation catheter with a balloon, 30 . . . water tank, 31 . . . counter electrode plate, 32 . . . pseudo affected tissue, 33 . . . Type T thermocouple, 34 . . . temperature data logger, 51a, 51b, 51c, 51d, 51e . . . bent portion, 52a, 52b . . . curved portion

The invention claimed is:

1. An ablation catheter system with a balloon, comprising:
   an ablation catheter;
   a balloon fixed to a front side of the ablation catheter, wherein the balloon is heated for ablation; and
   a guidewire configured for use with the ablation catheter and the balloon;
   wherein the guidewire comprises:
      a deformed portion formed by bending and/or curving the guidewire in a 20 to 100-mm region from an end portion in a longitudinal direction of the guidewire,
      a guidewire front end straight portion, which has a linear shape, positioned closer to said end portion than the deformed portion of the guidewire
   wherein, as for the deformed portion, a shortest distance between a central axis in the longitudinal direction of the guidewire and a point farthest away from the central axis in a direction perpendicular to the central axis is equal to or longer than a shortest inner diameter of a lumen of a catheter shaft of the ablation catheter with the balloon to be used with the guidewire and 40 mm or shorter,
   wherein the deformed portion of the guidewire is configured to prevent the end portion of the guidewire from approaching the front side of the ablation catheter to prevent erroneous heating of the end portion of the guidewire.

2. The ablation catheter system of claim 1, wherein the deformed portion of said guidewire is formed by bending and/or curving the guidewire 2 to 8 times.

3. The ablation catheter system of claim 1, wherein the deformed portion of said guidewire is in a spiral shape, a coiled shape, or a lasso shape.

4. The ablation catheter system of claim 1, wherein the deformed portion of said guidewire is provided with a potential measuring electrode.

* * * * *